US007105648B1

(12) United States Patent
Bock et al.

(10) Patent No.: US 7,105,648 B1
(45) Date of Patent: Sep. 12, 2006

(54) OLIGOMERS SUBSTITUTED BY PHOSPHITE ACID ESTER, PHOSPHONIC ACID OR CARBABORANE FUNCTIONS AND THE CORRESPONDING PNA MONOMERS

(75) Inventors: Holger Bock, Munich (DE); Thomas Lindhorst, Wasserburg (DE)

(73) Assignee: Ugichem GmbH, Innsbruck (AU)

( * ) Notice: Subject to any disclaimer, the term of this patent is extended or adjusted under 35 U.S.C. 154(b) by 0 days.

(21) Appl. No.: 09/914,052

(22) PCT Filed: Mar. 3, 2000

(86) PCT No.: PCT/EP00/01852

§ 371 (c)(1),
(2), (4) Date: Nov. 20, 2001

(87) PCT Pub. No.: WO00/52038

PCT Pub. Date: Sep. 8, 2000

(30) Foreign Application Priority Data

Mar. 3, 1999 (DE) ................................ 199 09 373

(51) Int. Cl.
*C07H 21/02* (2006.01)
*C07H 21/04* (2006.01)
*A01N 55/08* (2006.01)
*A61K 31/69* (2006.01)

(52) U.S. Cl. .................. 536/23.1; 536/17.1; 536/22.1; 536/25.6; 536/26.1

(58) Field of Classification Search .................... 514/2, 514/7, 8, 42, 43, 44, 52, 64; 536/1.11, 22.1, 536/23.1, 25.6, 26.1, 24.5, 17.1
See application file for complete search history.

(56) References Cited

U.S. PATENT DOCUMENTS 5,846,741 A * 12/1998 Griffiths et al. .............. 435/7.5

FOREIGN PATENT DOCUMENTS

WO    WO 98/42735    10/1998

OTHER PUBLICATIONS

Egholm, Michael et al., "Peptide Nucleic Acids (PNA). Oligonucleotide Analogues with an Achiral Peptide Backbone," Journal of the American Chemical Society, 1992, 114 (5), 1895-1897.*
Kane, Robert R. et al., "Solution-Phase Segment Synthesis of Boron-Rich Peptides," Journal of Organic Chemistry, 1993, 58 (5), 991-992.*
Varadarajan, Aravamuthan et al., "Novel Carboranyl Amino Acids and Peptides: Reagents for Antibody Modification and Subsequent Neutron-Capture Studies," 1991, 2 (4), 242-253.*

* cited by examiner

*Primary Examiner*—Patrick Lewis
(74) *Attorney, Agent, or Firm*—Frommer Lawrence & Haug LLP; Ronald R. Santucci

(57) ABSTRACT

The invention relates to novel oligomers containing PNA units that are substituted by phosphite ester, phosphonic acid, or carbaborane functions and PNA monomers that are substituted by phosphite ester, phosphonic acid, or carbaborane functions, from which the novel oligomers are produced.

6 Claims, No Drawings

OLIGOMERS SUBSTITUTED BY PHOSPHITE ACID ESTER, PHOSPHONIC ACID OR CARBABORANE FUNCTIONS AND THE CORRESPONDING PNA MONOMERS

The invention relates to novel oligomers containing PNA units substituted by phosphite ester, phosphonic acid, or carbaborane functions, and to PNA monomers substituted by phosphite ester, phosphonic acid, or carbaborane functions, from which the novel oligomers are produced.

It is known that peptidonucleic acids (PNAs) can bind to complementary nucleic acids (DNA or RNA) with greater affinity than their natural prototypes (M. Egholm, O. Buchardt, L. Christensen, C. Behrens, S. M. Freier, D. A. Driver, R. H. Berg, S. K. Kim, B. Norden, P. E. Nielsen, *Nature*, 1993, 365, 566–568, B. Hyrup, P. E. Nielsen, *Bioorg. Med. Chem.*, 1996, 4, 5–23).

However, the ability of hitherto known PNA oligomers to permeate into cells is very low compared with DNA or RNA. The usefulness of PNAs as antisense agents is greatly dependent on their intracellular availability, however.

Thus it is the object of the present invention to provide oligomers which, like PNAs, can bind to DNAs or RNAs whilst exhibiting improved ability to permeate into cells.

This object is achieved in the present invention by compounds of the formula

W-U-Z in which W may be a hydrogen atom or an amino acid unit or PNA unit.

U contains at least one unit of the formula Y and possibly one or more amino acid units and/or PNA units.

Z can be an OH function, an amino acid unit, or a PNA unit.

The inventors have found that the introduction of one or more phosphonic acid functions or phosphite ester functions, in particular, but alternatively the introduction of one or more carbaborane functions, into the side chain increases the cell-permeating ability of the PNA oligomers.

Y is a unit of the formula:

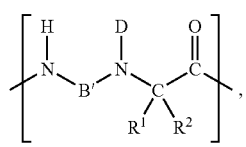

Y in which

B' denotes a group of the formula:

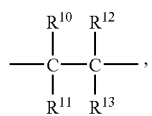

and

D denotes a group of the formula:

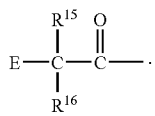

The residues $R^{10}$ to $R^{13}$ can independently contain up to 20 carbon atoms, preferably 1, 2, 3, 4, 5, 6, 7, 8, 9, or 10 carbon atoms. They can independently be hydrogen atoms, unsubstituted alkyl, alkenyl, alkaryl, aryl, or alicyclic groups, which groups may be branched or unbranched; these residues are preferably hydrogen atoms.

Optionally two of the residues $R^{10}$ to $R^{13}$, which are separated from each other by up to two carbon atoms, can in each case be components of a common ring system, this ring system being either an alicyclic monocyclic compound (3–8 ring atoms), that is unsubstituted or is substituted by a branched or unbranched $C_1$–$C_5$ alkyl group, or a phenyl ring; this ring system is preferably an unsubstituted cyclopentyl, cyclohexyl, or phenyl ring.

The residues $R^{15}$ and $R^{16}$ can independently contain up to 20 carbon atoms and preferably 1, 2, 3, 4, 5, 6, 7, 8, 9, or 10 carbon atoms. They are independently selected from the group comprising hydrogen atoms and unsubstituted alkyl, alkenyl, alkaryl, aryl, or alicyclic groups, said groups being branched or unbranched; more preferably, these residues are hydrogen atoms.

The residues $R^{15}$ and $R^{16}$ can optionally be components of a common ring system, this ring system being an alicyclic monocyclic compound (3–6 ring atoms) that is unsubstituted or substituted by a branched or unbranched $C_1$–$C_5$ alkyl group. This ring system is preferably an unsubstituted cyclohexyl ring or a cyclopentyl ring.

Throughout this application, the alkyl groups can be, for example, methyl, ethyl, propyl, or butyl groups.

E can be a natural or synthetic nucleobase optionally substituted by protecting groups, such as $X^1$ to $X^4$. Such nucleobases are capable of forming Watson-Crick or Hoogsteen base pairs.

Preferably, E can be a group of one of the following formulas:

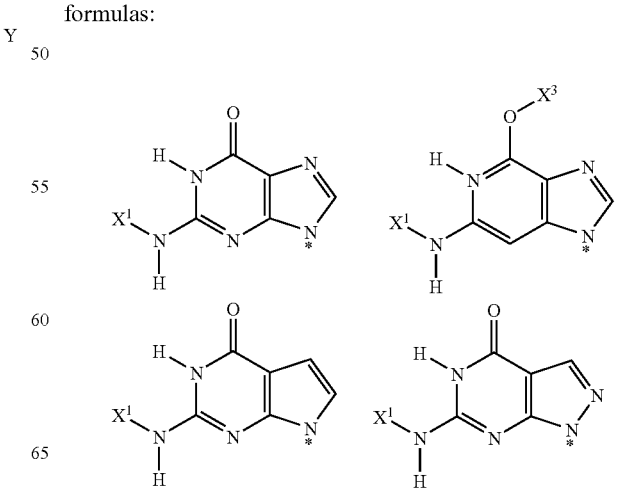

-continued

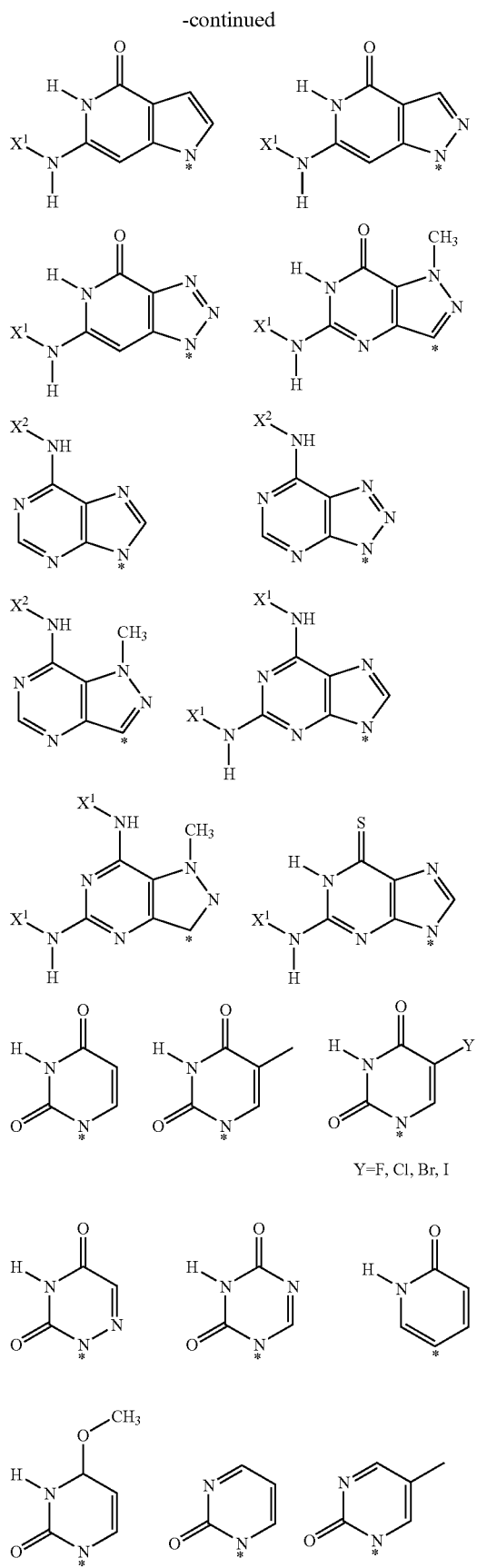

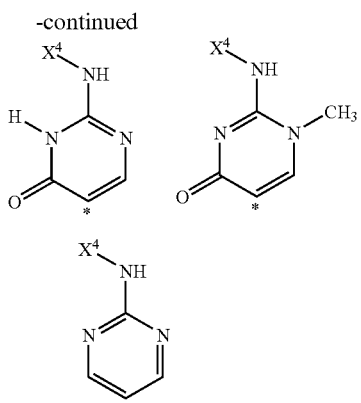

* substitution site in which $X^1$ to $X^4$ can independently be hydrogen atoms or one of the following substituents known from the technology of protecting groups for nucleobases:

$X^1$, $X^2$, and $X^4$: acetyl (Ac), isobutyryl (iBu—CO), carbobenzoxy (Cbz), (4-methoxyphenyl)diphenylmethyl (Mmt), benzhydryloxycarbonyl (Bhoc), and anisoyl (An), 4-tert-butylbenzoyl (tBuBz).

$X^3$: benzyl (Bn), diphenylcarbamoyl (Dpc).

Most preferably, E is selected from:

$N^2$-acetylguaninyl, $N^2$-isobutyrylguaninyl, $N^2$-benzyloxycarbonylguaninyl, $N^2$-(4-methoxyphenyl)diphenylmethylguaninyl, $N^2$-benzhydryloxycarbonylguaninyl, $N^6$-benzyloxycarbonyladeninyl, $N^6$-(4-methoxyphenyl)diphenylmethyladeninyl, $N^6$-anisoyladeninyl, $N^6$-benzhydryloxycarbonyladeninyl, $O^6$-benzylguaninyl ($X^1$ is a hydrogen atom), $N^2$-acetyl-$O^6$-diphenylcarbamoylguaninyl, $N^2$-isobutyryl-$O^6$-diphenylcarbamoylguaninyl, $N^2$-benzyloxycarbonyl-$O^6$-diphenylcarbamoylguaninyl, $N^2$-(4-methoxyphenyl)diphenylmethyl-$O^6$-diphenylcarbamoylguaninyl, $N^2$-benzhydryloxycarbonyl-$O^6$-diphenylcarbamoylguaninyl, $N^4$-benzyloxycarbonylcytosinyl, $N^4$-(4-methoxyphenyl)diphenylmethylcytosinyl, $N^4$-4-tert-butylbenzoylcytosinyl, $N^4$-benzhydryloxycarbonylcytosinyl, $N^2$-benzyloxycarbonyl-pseudoisocytosinyl, $N^2$-(4-methoxyphenyl)diphenylmethyl-pseudoisocytosinyl, $N^2$-4-tert-butylbenzoyl-pseudoisocytosinyl, $N^2$-benzhydryloxycarbonyl-pseudoisocytosinyl, adeninyl, cytosinyl, pseudoisocytosinyl, guaninyl, thyminyl, or uracinyl residue.

Most preferably, E is an adeninyl, cytosinyl, pseudoisocytosinyl, guaninyl, thyminyl, or uracilyl residue.

The residues $R^1$ and $R^2$ can independently be H-substituted alkyl, alkenyl, alkaryl, aryl, or alicyclic groups containing up to 20 carbons, whilst at least one of the residues $R^1$ or $R^2$ exhibits one or more phosphite ester, phosphonic acid, or carbaborane functions.

Phosphonic acid functions can have, for example, the formula —P(=O)(OH)$_2$.

Phosphite ester functions can have, for example, the formula —P(=O)(OV)$_2$ or P(=O)(OV)(OH). V can be an unsubstituted alkyl, alkenyl, alkaryl, aryl, or alicyclic group containing up to 20 carbons, more preferably up to 7 carbon atoms, and is most preferably a methyl, ethyl, or benzyl group.

Carbaborane functions containing up to 20 boron atoms—in particular up to 12, 10 or 8 boron atoms—and from 1 to 4 carbon atoms are preferred, known carbaborane functions being particularly preferred.

Preferably, the residues $R^1$ or $R^2$ contain 1, 2, 3, 4, 5, 6, 7, 8, 9, or 10 carbon atoms and are defined as above.

The residues $R^1$ and $R^2$ can be branched or unbranched. Most preferably, the residues $R^1$ and $R^2$ are defined as above whilst at least one of $R^1$ and $R^2$ is or contains a substituent of a synthetic amino acid.

Very preferably, the residues $R^1$ and $R^2$ are independently selected from the group comprising hydrogen atoms and units of formulas —$CH_2$—[P(=O)(O—K)$_3$] and —$CH_2$—C(CH$_3$)$_2$—[P(=O)(O—K)$_2$], K being a hydrogen atom or a methyl, ethyl, or benzyl group.

PNAs are optionally substituted oligomers having a N-(2-aminoethyl)glycine backbone. The substituent NB is a nucleobase.

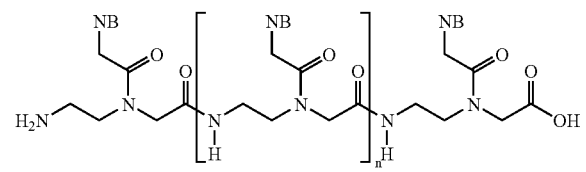

PNA oligomers are produced by linking peptide bonds between substituted N-acetyl-n-(2-aminoethyl)glycine building blocks (PNA monomers). In the oligomer, each of these substituted N-acetyl-n-(2-aminoethyl)glycine building blocks is a PNA unit. In the present invention, PNA units known per se can be used, units of the above formula being preferred.

Preferably, the compound W-U-Z is composed of up to 50, more preferably up to 40, and most preferably up to 30, of these units W, U and Z. For example, such compounds W-U-Z can contain up to 5 units of formula W, up to 30 units of formula U and up to 10 units of formula Z.

More preferably, W is a hydrogen atom, U comprises one or more units of formula Y and one or more PNA units, and Z is an OH group.

Most preferably, W is a hydrogen atom, U one or more units of formula Y, and Z an OH group.

If the oligomers contain carbaborane functions, they can be used in a boron neutron capture therapy (BNCT) for controlling cancerous tumors. BNCT involves the transfer of boron-containing molecules into cancer cells. The cells are then bombarded with slow neutrons, by which means the boron atoms decompose to high-energy particles and irreversibly destroy the surrounding tissue (*Chemie in unserer Zeit* 1997, 31*st Year of Issue No.* 5, 235). In BNCT work, boron-containing amino acids, sugars, porphyrins, phospholipides, thiouracil derivatives, nucleotide analogs, and nucleosides have been synthesized and examined (M. F. Hawthorne, *Angew. Chem.* 1993, 105, 997).

In the present invention, U can be an oligopeptide made up of amino acid units and/or PNA units and at least one unit of formula Y linked together in any order.

The oligomers of the invention can be produced, for example, by means of processes described in the literature by conversion of compounds of the general formula II in known manner (eg, L. Christensen, R. Fitzpatrick, B. Gildea, K. H. Petersen, H. F. Hansen, T. Koch, M. Egholm, O. Buchaedt, P. E. Nielsen, J. Coull, R. H. Berg, *J.Pept.Sci.* 1995, 1, 175–183, T. Koch, H. F. Hansen, P. Andersen, T. Larsen, H. G. Batz, K. Otteson, H. Oerum, *J.Pept.Res.* 1997, 49, 80–88, F. Bergmann, W. Bannwarth, S. Tam, *Tetrahedron Lett.* 1995, 36, 6823–6826)

In the compounds of the general formula II

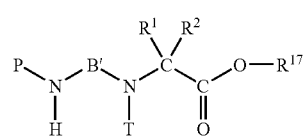

II

B' is as defined above,
T is a hydrogen atom or a group of the formula

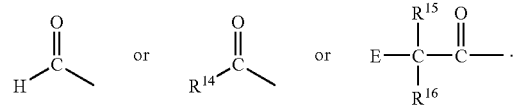

The residue $R^{17}$ can be a hydrogen atom or an allyl, benzyl, ethyl, methyl, 2,2,2-trichloro-tert-butyl, 2,2,2-trichloroethyl, α-chloro(trifluoromethyl)benzyl, 2-(p-toluenesulfonyl)ethyl, diphenylmethyl, 2-(trimethylsilyl)ethyl, methoxymethyl, (2-trimethylsilyl)ethoxymethyl, benzyloxymethyl, or (2-methoxy)ethyloxymethyl group.

When the residue $R^{17}$ is not a hydrogen atom, it can be bound to a solid phase. A suitable solid phase comprises any conventional solid-phase resin as used in organic solid-phase synthesis, and polystyrene-divinylbenzene resins, polyethylene glycol resins or polyethylene glycol polystyrene resins are preferred.

P can be a hydrogen atom or a cleavable amine protecting group. The amine protecting group must be selectively cleavable in the presence of the nucleobase protecting groups $X^1$ to $X^4$. Preferably, P is a hydrogen atom, an oxocarbamate or thiocarbamate protecting group, and more preferably, a hydrogen atom or an Fmoc, Boc, Cbz, Mmt or Bhoc protecting group.

The residue $R^{14}$ can be a group of formula $CH_nX_{3-n}$ (n=0 to 3, X=F, Cl, Br, I), phenyl or p-methoxyphenyl.

E, the residues $R^1$ and $R^2$, and $R^{15}$ and $R^{16}$ have the meanings stated above.

The compounds of the general formula II can, for example, be produced from compounds of the general formula I by known methods (PCT/EP 98/04622).

The synthesis of compounds of the general formula I is effected by means of the Ugi reaction (U 4CR), for example, according to the following reaction diagram:

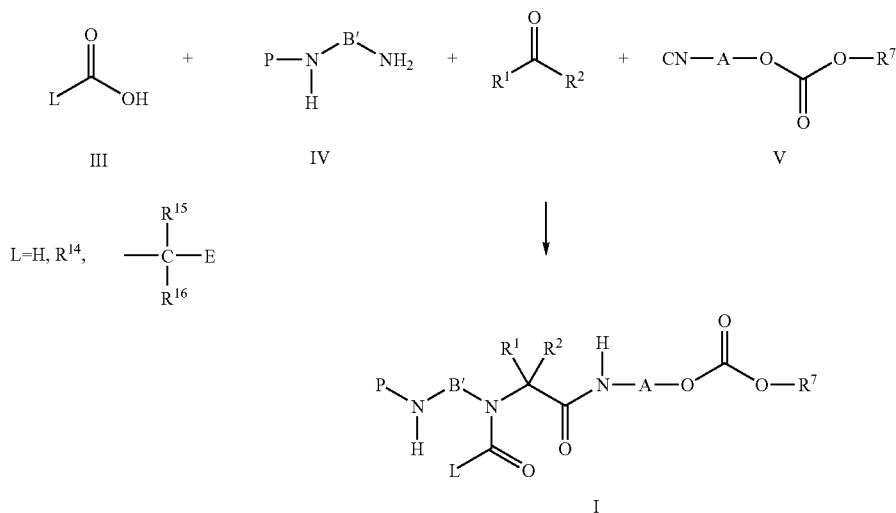

The reaction can be carried out, for example, as described in the literature (I. Ugi et al., *Chem. Ber.*, 1961, 94, 2802).

The nucleobase acetic acid components E-C($R^{15}R^6$)-COOH are produced as described in the literature (E. Uhlmann, A. Peyman, G. Breipohl, D. W. Will, *Angew. Chem.*, 1998, 110, 2954–2983).

The amine components of the general formula IV are produced, eg, by the Krapcko method (A. P. Krapcko, C. S. Kuile, *Synthetic Communications,* 1990, 20(16), 2559–2564).

The isocyanide components of the general formula V can be produced by any of the processes disclosed in patent application Ser. No. PCT/EP 98/04622. The processes are suitable for both resinbonded isocyanide components and non-resin-bonded isocyanide components.

The compounds of the general formula I are then converted, eg by the process described in the literature (Th. Lindhorst, H. Bock, I. Ugi, *Tetrahedron* 1999, 55, 7411–7420; PCT/EP 98/04622) to give the compounds of the general formula II. This is carried out, eg, by the addition of an equimolar amount of a nucleophilic base, such as potassium tert-butanolate, to the compounds of the general formula I in an aprotic solvent, for example as demonstrated by the following diagram:

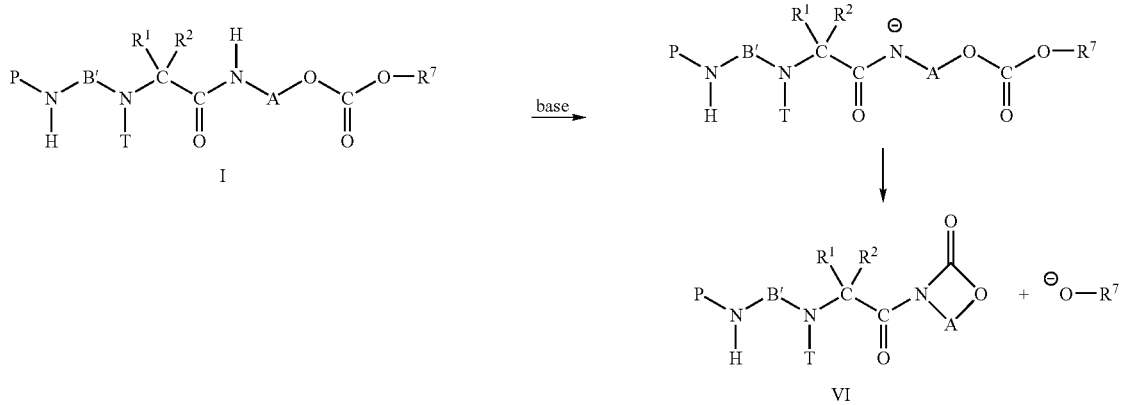

In the compounds of the general formula I

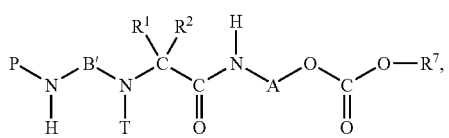

the groups B', T, P, and residues $R^1$ and $R^2$ have the same meanings as stated for the compounds of the general formula II.

The residue $R^7$ has the same meaning as stated for residue $R^{17}$ in the compound of the general formula II or may be a phenyl group but not a hydrogen atom.

A can be a group of the formula —C($R^3$,$R^4$)—C($R^5$, $R^6$)—, in which the residues $R^3$ to $R^6$ are independently hydrogen, phenyl, or methyl.

This process is particularly well suited for the generation of novel PNA monomers whose side chains correspond to those of unnatural amino acids. Hitherto known procedures involved the elaborate production of the synthetic amino acid for this purpose. Following basic cleavage of the C-terminal protecting group, the base-stable protecting group P can be optionally replaced by a base-labile protecting group P (eg, Fmoc).

If the residue $R^7$ lowers the nucleophilicity of the oxygen atom bound thereto (when $R^7$ is, eg, a phenyl group), the intermediate products VI are isolable (cf patent application Ser. No. PCT/EP 98/04622). VI can then be converted by mild basic hydrolysis to the compounds of the general formula II, in which $R^{17}$ is a hydrogen atom.

If, in the compounds of the general formula I, the residue $R^7$ does not lower the nucleophilicity of the oxygen atom bound thereto, the intermediate products VI are not isolable. In such cases, VI reacts in situ with the alkoxides (Alkoholation) formed by the intramolecular ring closure to give the corresponding esters of the general formula II, for example as shown by the following diagram.

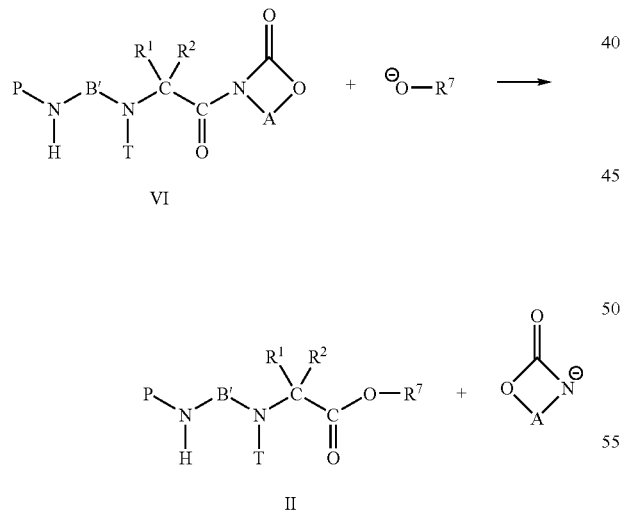

Following the basic cleavage of the C-terminal protecting group, it is possible to remove a base-stable protecting group P as defined above (eg, Boc) in the compounds of the general formula II by commonly used methods and to optionally replace it by a new protecting group selectively cleavable in the presence of the nucleobase protecting groups $X^1$ to $X^4$ (eg, the base-labile protecting group Fmoc).

BEISPIELE

EXAMPLE 1

Production of

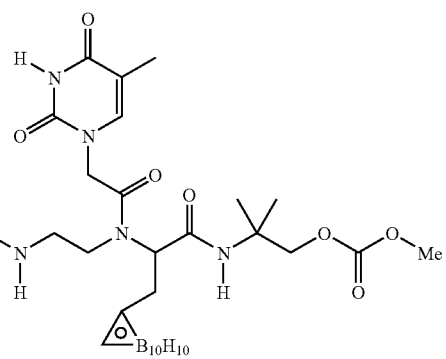

5 mmol each of thyminyl acetic acid, 2-(1,2-dicarbaclosododecaborone)ethanal, N-Boc ethylene diamine, and methyl 2-isocyano-2,2-(dimethyl)ethylcarboxylate are dissolved in 50 mL of trifluoroethanol and stirred at 25° C. On completion of the reaction, the solvent is removed.

The reaction mixture is purified by column chromatography. The reaction product is obtained in 70% yield.

EXAMPLE 2

Production of

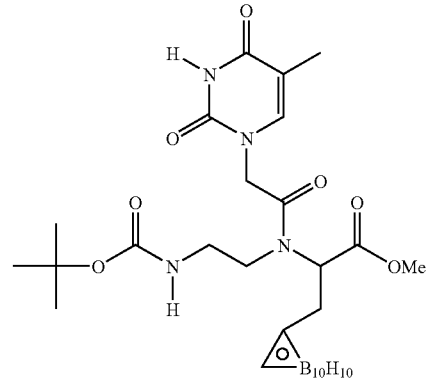

2 mmol of the reaction product of Example 1 are dissolved in 10 mL of absolute THF, and 2 mmol of sodium hydride are added at 25° C. On completion of the reaction, the reaction mixture is filtered through a short silica gel column. The solvent is removed and the reaction product purified by column chromatography. The reaction product is obtained in a yield of 70%.

EXAMPLE 3

Production of

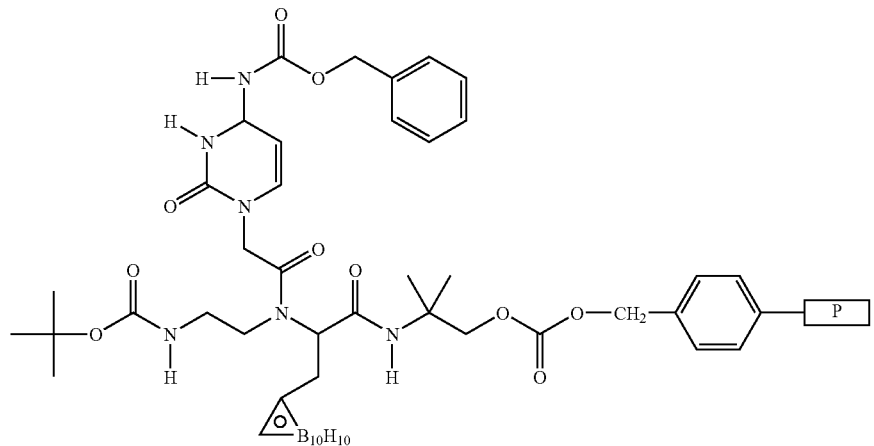

5 mmol each of ($N^4$-Cbz-cytosyl) acetic acid, 2-(1,2-dicar-baclosododecaborane)ethanal, N-Boc ethylene diamine, and methylpolystyrene 2-isocyano-2,2-(dimethyl)ethylcarboxylate are suspended in 50 mL of trifluoroethanol and stirred at 25° C. On completion of the reaction, the solvent is removed via a frit and the reaction mixture washed a number of times with methanol, dichloromethane, a pH 9 sodium hydrogencarbonate solution, and water.

The reaction product is obtained in a yield of 80% (determine by brometric detection of unconverted isocyanide resin).

EXAMPLE 4

Production of

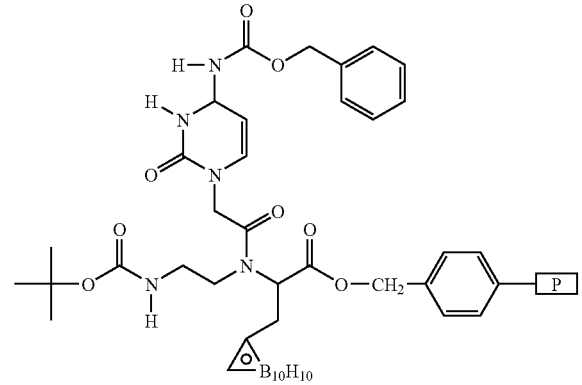

2 mmol of the reaction product of Example 3 are suspended in 10 mL of absolute THF, and 2 mmol of potassium tert-butanolate are added at 25° C. On completion of the reaction, the solvent is removed via a frit and the reaction mixture washed a number of times with methanol, dichloromethane, a pH 9 sodium hydrogencarbonate solution, and water.

The reaction product is obtained in a yield of 60%.

EXAMPLE 5

Production of

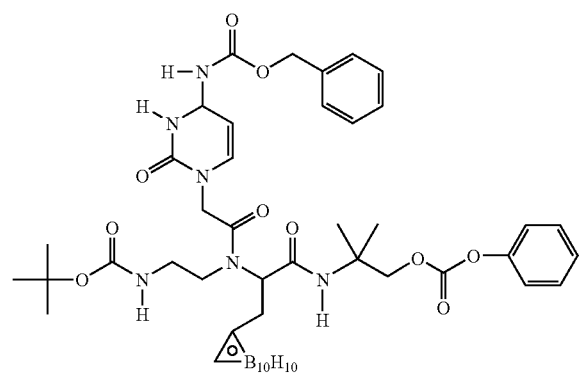

5 mmol each of ($N^4$-Cbz-cytosyl) acetic acid, 2-(1,2-dicar-baclosododecaborane)ethanal, N-Boc ethylene diamine, and phenyl 2-isocyano-2,2-(dimethyl)ethylcarboxylate are dissolved in 50 mL of trifluoroethanol and stirred at 25° C. On completion of the reaction, the solvent is removed.

The reaction mixture is purified by column chromatography. The reaction product is obtained in 80% yield.

EXAMPLE 6

Production of

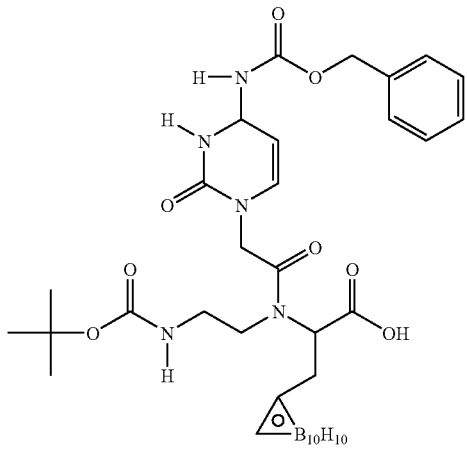

2 mmol of the reaction product of Example 5 are dissolved in 10 mL of absolute THF, and 2 mmol of potassium tert-butanolate are added at 25° C. On completion of the reaction, an aqueous 1 M potassium hydroxide solution is added to the reaction mixture, which is stirred until no more conversion can be detected. The reaction solution is neutralized and the solvent removed. The reaction product is purified by column chromatography. The reaction product is obtained in a yield of 70%.

EXAMPLE 7

Production of

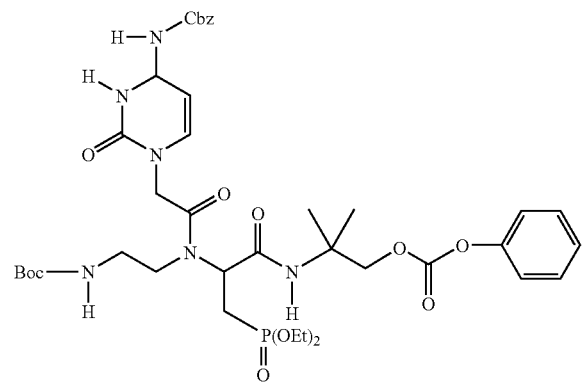

5 mmol each of ($N^4$-Cbz-cytosyl) acetic acid, diethyl 2-phosphite ester ethanal, N-Boc ethylene diamine, and phenyl 2-isocyano-2,2-(dimethyl)ethylcarboxylate are dissolved in 50 mL of ethanol. In order to improve the solubility properties of ($N^4$-Cbz-cytosyl) acetic acid, 5 mmol of triethylamine are added and the mixture is stirred at 25° C. On completion of the reaction, the solvent is removed.

The reaction mixture is purified by column chromatography. The reaction product is obtained in 70% yield.

EXAMPLE 8

Production of

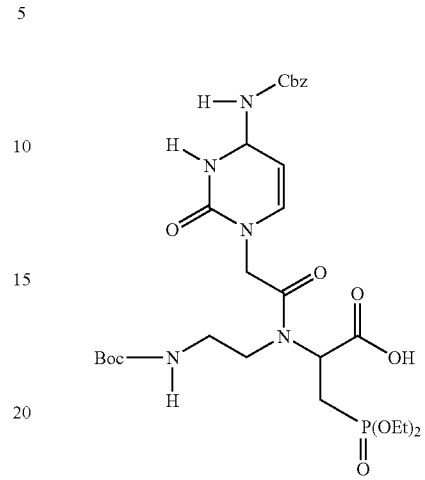

2 mmol of the reaction product of Example 7 are dissolved in 10 mL of absolute THF, and 2 mmol of potassium tert-butanolate are added at 25° C. On completion of the reaction, 2 mmol of potassium hydroxide as aqueous 1 M solution are added to the reaction mixture, which is stirred until no more conversion can be detected. The reaction solution is neutralized and the solvent removed. The reaction product is purified by column chromatography. The reaction product is obtained in a yield of 55%.

EXAMPLE 9

Production of

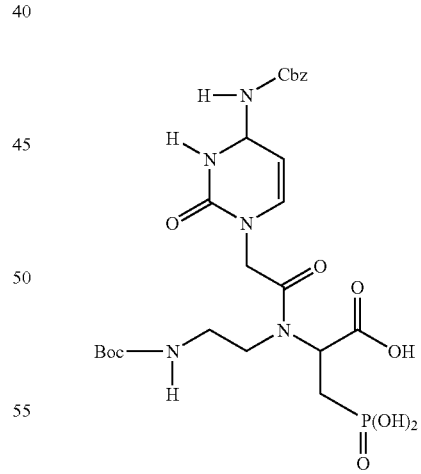

2 mmol of the reaction product of Example 8 are dissolved in 10 mL of absolute THF, and 2 mmol of potassium hydroxide as aqueous 1 M solution are added at 50° C. On completion of the reaction, the reaction solution is neutralized and the solvent removed.

The reaction product is purified by preparative HPLC. The reaction product is obtained in a yield of 40%.

EXAMPLE 10

Preparation of

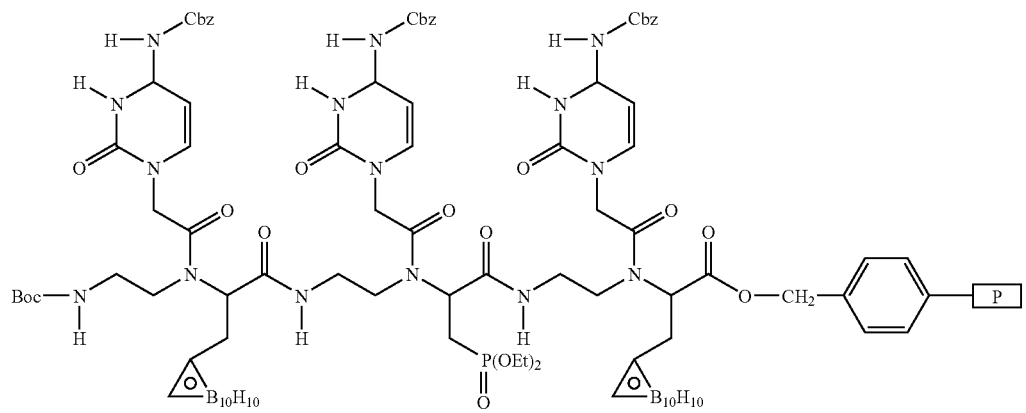

Synthesis Procedure

Step 1: 100 mg of the reaction product of Example 4 are presoaked in dichloromethane for 12 h, Step 2: deprotection with tert-butyloxycarbonyl in a peptide synthesizer using a 50% strength solution of trifluoroacetic acid in dichloromethane (1:1 v/v, 2 ml, 1×2 minutes, 1×30 min), Step 3: washing with dichloromethane (2 ml, 4×20 seconds), Step 4: neutralization with DIPEA/dichloromethane (1:19 v/v, 2 ml, 2×3 min), Step 5: washing with dichloromethane (2 ml, 2×20 seconds), washing with DMF (2 ml, 3×20 seconds), Step 6: addition of 4 equivalents of HBTU and diethylcyclohexylamine in DMF/pyridine (1:1 v/v) und 4 equivalents of the reaction product of Example 8, Step 7: washing with DMF (2 ml, 3×20 seconds) und dichloromethane (3 ml, 3×20 seconds), Step 8: capping with a solution of 0,5 M acetic anhydride/ 0,5 M DMF, Step 9: washing with DMF (2 ml, 3×20 seconds) und dichloromethane (3 ml, 3×20 seconds), Step 10: repetition of the synthesis cycle from Step 2, while in Step 6 4 equivalents of the reaction product of Example 6 are used instead of the reaction product of Example 8, Step 11: drying in a stream of nitrogen.

The product is obtained in a yield of 97%.

EXAMPLE 11

Production of

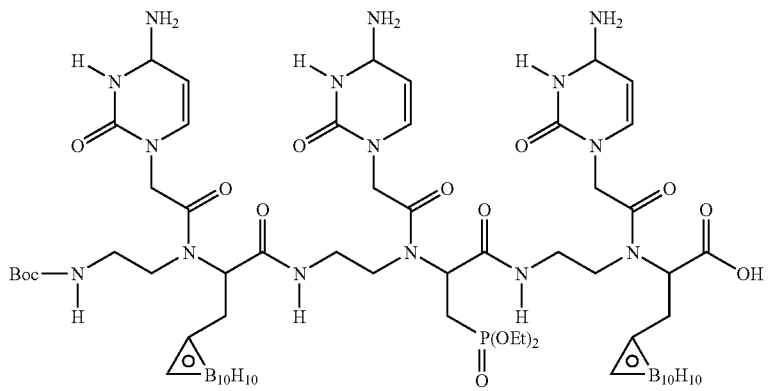

The reaction product of Example 10 is suspended in methanol, and a catalytic amount of platinum-on-carbon is added. The reaction mixture is hydrogenated under a blanket of hydrogen.

On completion of the reaction, the solvent is removed, and the product is purified by preparative HPLC. The reaction product is obtained in a yield of 96%.

EXAMPLE 12

Production of

[chemical structure]

The reaction product of Example 11 is suspended in dichloromethane. There are added 1 mL each of trifluoroacetic acid and thiophenol. On completion of the reaction, the reaction product is purified by preparative HPLC. The reaction product is obtained in a yield of 99%.

The invention claimed is:

1. A compound of the formula:

W-U-Z wherein:

W is a hydrogen atom, an amino acid, or a PNA, U contains at least one unit of the formula Y and, optionally, one or more amino acid and/or PNA, Z is an OH function, an amino acid, or a PNA, Y is a unit of the formula

[structure Y]

wherein:

B' is a group of the formula:

[structure with $R^{10}, R^{11}, R^{12}, R^{13}$]

D is a group of the formula:

[structure with E—C($R^{15}$)($R^{16}$)—C(=O)—]

wherein the residues $R^{10}$ to $R^{13}$ independently contain up to 20 carbon atoms and independently denote hydrogen atoms or unsubstituted alkyl, alkenyl, alkaryl, aryl, or alicyclic groups, said groups being branched or unbranched, and optionally two each of the residues $R^{10}$ to $R^{13}$, separated from each other by up to two carbon atoms, are components of a common ring system, which ring system is either an alicyclic monocyclic compound comprising 3–8 ring atoms, optionally substituted by a branched or unbranched $C_{1-5}$ alkyl group, or a phenyl ring, the residues $R^{15}$ and $R^{16}$ independently contain up to 20 carbon atoms and independently denote hydrogen atoms or unsubstituted alkyl, alkenyl, alkaryl, aryl, or alicyclic groups, said groups being branched or unbranched, and optionally the residues $R^{15}$ and $R^{16}$ are components of a common ring system, which ring system is an alicyclic monocyclic compound comprising 3–6 ring atoms, optionally substituted by a branched or unbranched $C_{1-5}$ alkyl group, E is a natural or synthetic nucleobase, optionally substituted by protecting groups and capable of forming Watson-Crick or Hoogsteen base pairs, and the residues $R^1$ and $R^2$ are independently hydrogen atoms, alkyl, alkenyl, alkaryl, aryl, or alicyclic groups containing up to 20 carbons, whilst at least one of the residues $R^1$ and $R^2$ is one or more phosphite ester, phosphonic acid, or carbaborane functions.

2. The compound according to claim 1, wherein W is a hydrogen atom, U is one or more units of formula Y, and Z is an OH group.

3. The compound according to claim 1, wherein at least one of the residues $R^1$ and $R^2$ exhibits one or more phosphite ester or phosphonic acid functions.

4. The compound according to claim 1, wherein at least one of the residues $R^1$ and $R^2$ exhibits one or more carbaborane functions.

5. A compound of the general formula II:

[structure II]

wherein T is hydrogen or a group of the formula:

[three structures]

the residue $R^{17}$ is hydrogen or allyl, benzyl, ethyl, methyl, 2,2,2-trichloro-tert-butyl, 2,2,2-trichloroethyl, α-chloro-(trifluoromethyl)benzyl, 2-(p-toluenesulfonyl)ethyl, diphenyl-methyl, 2-(trimethylsilyl)ethyl, methoxymethyl, (2-trimethyl-silyl)ethoxymethyl, benzyloxymethyl, or (2-methoxy)ethyloxymethyl, the residue P is hydrogen or an amine protecting group, the residue $R^{14}$ is a group of the formula $CH_nX_{3-n}$, wherein n=0 to 3, and X=F, Cl, Br, or I, a phenyl group, or a p-methoxyphenyl group, and B', E, the residues $R^1$ and $R^2$, and $R^{15}$ and $R^{16}$ are defined as in claim 1.

6. The compound according to claim 5, wherein the amine protecting group is an Fmoc, Boc, Cbz, Mmt, or Bhoc protecting group.

* * * * *